(12) United States Patent
Crozet et al.

(10) Patent No.: US 12,145,907 B2
(45) Date of Patent: *Nov. 19, 2024

(54) PROCESS FOR PREPARING DIESTERS FROM UNSATURATED FATTY ALCOHOLS AND DIESTERS THUS OBTAINED

(71) Applicant: TOTALENERGIES ONETECH, Courbevoie (FR)

(72) Inventors: Delphine Crozet, Villeurbanne (FR); Alice Limoges, Ternay (FR)

(73) Assignee: TOTALENERGIES ONETECH, Courbevoie (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/785,603

(22) PCT Filed: Dec. 18, 2020

(86) PCT No.: PCT/FR2020/052521
§ 371 (c)(1),
(2) Date: Jun. 15, 2022

(87) PCT Pub. No.: WO2021/123656
PCT Pub. Date: Jun. 24, 2021

(65) Prior Publication Data
US 2023/0091311 A1    Mar. 23, 2023

(30) Foreign Application Priority Data

Dec. 20, 2019 (FR) ...................................... 1915157

(51) Int. Cl.
*C07C 67/08* (2006.01)
*A61K 8/37* (2006.01)
*C10M 105/38* (2006.01)

(52) U.S. Cl.
CPC ................ *C07C 67/08* (2013.01); *A61K 8/37* (2013.01); *C10M 105/38* (2013.01)

(58) Field of Classification Search
CPC ............ C10N 2040/02; C10N 2030/74; C10N 2040/25; C10N 2030/10; C10N 2070/00; C10N 2030/02; C10N 2030/12; C10N 2040/20; C10N 2040/04; C10M 129/74; C10M 177/00; C10M 105/38; C10M 2207/2835; C10M 2207/283; C07C 67/04; C07C 67/08; C07C 69/24; A61Q 19/00; A61K 47/14; A61K 8/37; A61K 9/06

See application file for complete search history.

(56) References Cited

U.S. PATENT DOCUMENTS

| | | | |
|---|---|---|---|
| 5,008,126 A | 4/1991 | Klemann | |
| 6,491,927 B1 | 12/2002 | Arnaud | |
| 2010/0120642 A1 | 5/2010 | Miller | |
| 2011/0009300 A1 | 1/2011 | Elomari | |
| 2015/0232410 A1* | 8/2015 | Bertin | C07C 69/24 508/505 |
| 2015/0247104 A1 | 9/2015 | Brekan | |

FOREIGN PATENT DOCUMENTS

JP    S36-13069    8/1961

OTHER PUBLICATIONS

Douguet, M., et al., "Spreading properties of cosmetic emollients: Use of synthetic skin surface to elucidate structural effect," Colloids and Surfaces B; Biointerfaces, vol. 154 (Mar. 16, 2017) pp. 307-314.

* cited by examiner

*Primary Examiner* — Vishal V Vasisth
(74) *Attorney, Agent, or Firm* — DUANE MORRIS LLP; Gregory M. Lefkowitz; Brandon A. Chan

(57) ABSTRACT

The invention relates to a method for preparing a composition of diesters comprising reacting an unsaturated compound of alcohol type or the ester thereof, with a saturated fatty acid, in the presence of an acid catalyst. The invention also relates to a composition of diesters that is obtainable by the method of the invention, and the use thereof in lubricating compositions or in cosmetic or pharmaceutical compositions.

15 Claims, No Drawings

PROCESS FOR PREPARING DIESTERS FROM UNSATURATED FATTY ALCOHOLS AND DIESTERS THUS OBTAINED

CROSS-REFERENCE TO RELATED APPLICATIONS

This application is a § 371 national stage entry of International Application No. PCT/FR2020/052521, filed on Dec. 18, 2020, which claims priority to French Patent Application No. 1915157, filed on Dec. 20, 2019, the entire contents of which are incorporated herein by reference.

The invention relates to a method for preparing diesters from one or more unsaturated fatty alcohol(s).

The invention also relates to a diester composition of one or more diester(s) that is obtainable by the method according to the invention and may be used in lubricating compositions or cosmetic or pharmaceutical compositions.

STATE OF THE ART

Lubricating compositions, also known as lubricants, are widely used in order to reduce friction between the surfaces of moving parts and thus reduce wear and prevent degradation or damage to the surface of these parts. The lubricants typically include a base oil and one or more functional additives.

When the lubricating composition is subjected to high stresses (ie high pressures) during its use, the lubricating compositions wherein the base oil consists of hydrocarbons tend to break down causing the parts to then get damaged.

Manufacturers of lubricants must constantly improve their formulations in order to respond to increased demands with respect to fuel economy while also maintaining engine cleanliness and reducing emissions. Given these requirements manufacturers are obliged to reassess their formulation capabilities and/or to undertake research to seek out new base oils that are capable of satisfying stringent performance requirements.

In order to manufacture lubricants, such as engine oils, transmission fluids, gear oils, industrial lubricating oils, metalworking oils, etc, one typically starts with a petroleum-based oil of lubricating grade derived from a refinery, or from a suitable polymerised petrochemical fluid. In this base oil, small amounts of additives are blended therein so as to enhance the properties and performance thereof, such as augmenting of lubricity, anti-wear and anti-corrosion properties, and the resistance of the lubricant to heat and/or oxidation. Thus, various additives such as antioxidants, corrosion inhibitors, dispersing agents, antifoaming agents, metal deactivators and other additives that can be used in lubricant formulations may be added in conventional effective amounts.

In the American Petroleum Institute (API) Classification of Base Oils, esters are referred to as Group V base oils. Synthetic esters may be used both as a base oil and as an additive in lubricants. In comparison to cheaper but less environmentally safe mineral oils, synthetic esters were mainly used as base oils in cases where there were strict requirements in respect of the viscosity/temperature behaviour that had to be met. The increasingly important issues of environmental acceptability and biodegradability are driving the desire to find alternatives to mineral oil as a raw material in lubrication applications.

The cosmetics, dermatology and pharmaceutical markets are increasingly demanding biologically derived (or bio-based) ingredients for the formulation of their products.

While active ingredients, emulsifiers and plant oils that are bio-based, have seen significant development in recent years and are now widely available on the market, emollients that are 100% organically-sourced are still rare.

The emollients currently used in cosmetics are either isoparaffins derived from petrochemicals (mainly isododecane and isohexadecane), white oils, silicone oils or ester-based oils (synthetic or natural). Isoparaffins, white oils and silicone oils are widely distributed because they are very stable and odourless but are not derived from renewable resources. Although volatile silicones such as cyclomethicone have long been considered to be emollients and solvents that are harmless to the skin (International Journal of Toxicology, Vol. 10, No 1, pp 9-19, 1991), concerns have been expressed in recent years concerning their potential deleterious effects on the environment, and even on human health (in particular with regard to octamethylcyclotetrasiloxane).

Environmental restrictions and concerns continue to lead manufacturers to seek alternatives to sources that are petroleum based (fossil). Oils of plant or animal origin have therefore proven to be interesting sources of base oils or emollients. In particular, these oils of plant or animal origin may be converted into an acid or an ester by conventional methods. These acids may then be converted into unsaturated alcohols, for example from triglyceride oil, by means one or more hydrogenation steps of hydrogenating the fatty acids or methyl esters.

The document US 2010/120642 discloses lubricating compositions based on diesters obtained via an epoxy intermediate. The document U.S. Pat. No. 5,008,126 discloses diol diesters, in which the ester functional groups are separated by one or two methylene groups. These diol diesters are used as a fat substitute in food.

The invention thus aims to provide a composition of diesters with high selectivity towards diesters and in particular towards a specifically targeted diester, with this being accompanied by a high conversion rate. This composition of diesters may also be obtained from raw materials derived from plant or animal sources.

SUMMARY OF THE INVENTION

The invention relates to a method for preparing a composition of diesters comprising at least one addition reaction of an acid functional group of at least one saturated fatty acid containing from 2 to 18 carbon atoms onto a carbon-carbon double bond of at least one unsaturated compound selected from among an unsaturated alcohol containing from 11 to 20 carbon atoms, an ester of a saturated fatty acid containing from 2 to 18 carbon atoms and an unsaturated alcohol containing from 11 to 20 carbon atoms, or a mixture thereof, in the presence of at least one acid catalyst.

According to one embodiment, the unsaturated alcohol is a monounsaturated monoalcohol containing from 11 to 18 carbon atoms, preferably from 14 to 18 carbon atoms and/or the saturated fatty acid, implemented for the addition reaction and/or of the acid part of the unsaturated compound in ester form, is a mono fatty acid containing from 2 to 16 carbon atoms, preferably from 7 to 12 carbon atoms.

According to one embodiment, the unsaturated compound comprises at least one unsaturated alcohol, the said method comprising the following two reactions:

a) Esterification reaction causing esterification of at least one unsaturated alcohol containing from 11 to 20 carbon atoms with at least one saturated fatty acid, either linear or branched, preferably branched, containing from 2 to 18 carbon atoms, in order to obtain at least one ester of the unsaturated alcohol; and b) Addition reaction causing addition of at least one saturated fatty acid, either linear or branched, preferably linear, containing from 2 to 18 carbon atoms, on the carbon-carbon double bond of the one or more unsaturated alcohol ester(s) obtained at the end of step a).

According to one embodiment, the addition reaction causing addition of the saturated fatty acid to the unsaturated compound, preferably the ester of the unsaturated alcohol, is carried out in accordance with one or more of the following conditions:

at a temperature ranging from 20 to 90° C., preferably from 30 to 85° C., more preferably from 40 to 80° C.; and/or at atmospheric pressure or under vacuum, preferably at atmospheric pressure; and/or a molar ratio of the unsaturated compound/saturated fatty acid ranging from 1/10 to 1/1, preferably from 1/8 to 1/2, more preferably ranging from 1/7 to 1/3; and/or a molar ratio of the unsaturated compound/catalyst ranging from 1/0.05 to 1/1, preferably from 1/0.1 to 1/0.8, more preferably from 1/0.15 to 1/0.5.

According to one embodiment of the method of the invention, the unsaturated compound is an unsaturated alcohol, the said method being implemented:

in one single batch step with introduction of the entirety of the saturated fatty acids implemented; or in two steps, including a first step of introducing a portion of the fatty acids, in order to carry out the esterification of the unsaturated alcohol(s), followed by a second step of introducing the rest of the saturated fatty acids, in order to carry out the addition reaction, preferably these two steps are implemented sequentially without separation of the esters obtained at the end of the esterification reaction.

The invention also relates to a composition of diesters (diester composition) that is obtainable by the method according to the invention.

According to one embodiment, the composition of diesters comprises at least one compound having the formula (1):

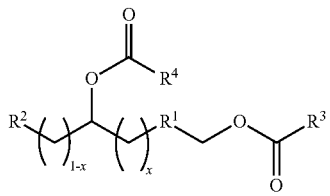

[Chem 1]

wherein:

$R^1$ is a linear or branched alkylene or alkenylene radical containing from 3 to 15 carbon atoms;

$R^2$ is a hydrogen atom or a linear or branched alkyl or alkenyl radical containing from 1 to 16 carbon atoms;

$R^3$ and R4 are, independently of each other, a linear or branched alkyl radical containing from 1 to 17 carbon atoms;

x is an integer equal to 0 or 1;

it being understood that the sum of the carbon atoms of the radicals $R^1$ and $R^2$ ranges from 8 to 17.

Preferably, in the compound having the formula (1):

$R^1$ is a linear alkylene radical containing from 3 to 15 carbon atoms;

$R^2$ is a hydrogen atom or a linear alkyl radical containing from 2 to 12 carbon atoms;

it being understood that the sum of the carbon atoms of the radicals $R^1$ and $R^2$ ranges from 8 to 16 carbon atoms;

$R^3$ is a branched alkyl radical containing from 3 to 9 carbon atoms;

$R^4$ is a linear alkyl radical containing from 3 to 17 carbon atoms;

x is an integer equal to 0 or 1.

The invention also relates to the use of the composition of diesters according to the invention, as a base oil in a lubricating composition or as an emollient in a cosmetic or pharmaceutical composition.

The object of the invention also relates to a lubricating composition comprising the composition of diesters according to the invention and at least one base oil and/or at least one additive, the said base oil and the said additive being other than the diesters according to the invention.

Finally, the invention relates to a cosmetic or pharmaceutical composition comprising the composition of diesters according to the invention and at least one fatty substance and/or at least one additive, the said fatty substance and the said additive being other than the diesters according to the invention.

The method of the invention provides the ability to obtain novel diesters from a raw material of a type such as unsaturated alcohol, it being possible for the said unsaturated alcohols to be obtained from biosourced and biodegradable products.

The novel diesters additionally also exhibit satisfactory properties in terms of rheological behaviour, physico-chemical properties and performance (with respect to friction, material compatibility, viscosity, storage stability and oxidation stability, anti-corrosion) for lubricating applications.

The novel diesters also exhibit enhanced sensory properties (feel, luster or gloss), that are suitable for topical applications, in particular for cosmetics, dermatological or pharmaceutical applications, on the skin, nails, lips, scalp or hair.

The composition of diesters according to the invention makes it possible to provide a non-irritant and biodegradable composition.

The composition of diesters according to the invention makes it possible to obtain stable topical compositions.

The composition of diesters according to the invention moreover exhibits an emollient nature with a soft and nourishing finish (feeling).

The composition of diesters according to the invention makes it possible to replace ingredients of such type as silicone, for example dimethicone or polyisobutenes, in topical compositions.

DETAILED DESCRIPTION OF THE INVENTION

The invention relates to a method for preparing a composition of diesters comprising at least one addition reaction of an acid functional group of at least one saturated fatty acid containing from 4 to 18 carbon atoms onto a carbon-carbon double bond of at least one unsaturated compound selected from among an unsaturated alcohol containing from 11 to 20 carbon atoms, an ester of a saturated fatty acid containing from 4 to 18 carbon atoms and an unsaturated alcohol containing from 11 to 20 carbon atoms, or a mixture thereof, in the presence of at least one acid catalyst.

The preparation method according to the invention may include the following steps:

a) Esterification of an unsaturated alcohol containing from 11 to 20 carbon atoms with at least one saturated fatty acid containing from 4 to 18 carbon atoms;

b) Addition reaction for addition of an acid functional group of at least one saturated fatty acid containing from 4 to 18 carbon atoms on a carbon-carbon double bond of one or more ester(s) of one or more saturated fatty acid(s) containing from 4 to 18 carbon atoms and of the unsaturated alcohol containing from 11 to 20 carbon atoms obtained in step a).

The two steps a) and b) detailed above may be implemented simultaneously with a batch addition of the entirety of the saturated fatty acids from steps a) and b), or sequentially with a sequential addition with: i) addition of the saturated fatty acids for the implementation of step a); and ii) addition of the saturated fatty acids for the implementation of step b). Alternatively, steps a) and b) may be implemented separately (two distinct batch steps) with separation/isolation of the unsaturated alcohol ester formed at the end of step a).

The method for preparing a composition of diesters according to the invention comprises in particular the reaction between an olefin functional group (carbon-carbon double bond) of an unsaturated compound of a type such as unsaturated alcohol or the ester thereof, and a carboxylic acid functional group of a saturated fatty acid. This reaction is also referred to as the addition reaction for adding the fatty acid to the unsaturated compound.

It should be noted that the method of the invention may include one or more distillation steps that provide the means to separate the saturated acid and/or the unsaturated compound, the starting reactant of the method of the invention, from the composition of diesters.

The method according to the invention may also include one or more washing steps for separating the homogeneous catalyst from the product resulting from the method of the invention; or one or more separation steps, for example by filtration, for separating the heterogeneous catalyst from the product resulting of the method of the invention.

By way of a preliminary stipulation, it will be noted that, in the description and the claims following thereafter, the expression "included between" shall be understood to be inclusive of the limits cited.

Unsaturated Alcohol or Ester Thereof

The method of the invention makes use of at least one unsaturated alcohol and/or one of the esters thereof (referred to as "unsaturated compound") as reactant for the reaction with the saturated fatty acid.

The unsaturated alcohol may be a linear or branched alcohol comprising one or more unsaturations, preferably one single unsaturation.

Preferably, the unsaturated alcohol is a linear alcohol comprising one single unsaturation.

Preferably, the unsaturated alcohol is a monoalcohol which comprises no other functional group other than the alcohol functional group and the carbon-carbon double bond.

In other words, preferably, the said at least one unsaturated alcohol is a monounsaturated monoalcohol.

Typically, the unsaturated alcohol is a primary unsaturated alcohol, i.e. including a structure of the type —CH$_2$—OH. Preferably, the carbon-carbon double bond is located neither in the alpha position nor in the beta position of the alcohol functional group. In other words, according to one preferred embodiment, the unsaturated alcohol comprises the structure —CH$_2$—CH$_2$—OH.

Preferably, the unsaturated alcohol contains from 11 to 18 carbon atoms, preferably from 14 to 18 carbon atoms.

According to one embodiment, the unsaturated alcohol corresponds to the formula (2):

[Chem 2]

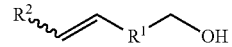

wherein:

R$^1$ is a linear or branched alkylene or alkenylene radical containing from 3 to 15 carbon atoms, preferably a linear or branched alkylene radical containing from 3 to 15 carbon atoms, more preferably a linear alkylene radical containing from 5 to 12 carbon atoms;

R$^2$ is a hydrogen atom or a linear or branched alkyl or alkenyl radical containing from 1 to 16 carbon atoms, preferably a hydrogen atom or a linear alkyl radical containing from 2 to 12 carbon atoms, more preferably a hydrogen atom or a linear alkyl radical containing from 4 to 10 carbon atoms;

it being understood that the sum of the carbon atoms of the radicals R$^1$ and R$^2$ ranges from 8 to 17 carbon atoms, preferably from 8 to 16 carbon atoms, more preferably from 11 to 16 carbon atoms.

According to one preferred embodiment, in the formula (2) above:

R$^1$ is a linear alkylene radical containing from 5 to 12 carbon atoms; and

R$^2$ is a hydrogen atom or a linear alkyl radical containing from 2 to 12 carbon atoms;

it being understood that in this particular embodiment, the sum of the carbon atoms of the radicals R$^1$ and R$^2$ ranges from 11 to 16 carbon atoms.

Positional isomers may also be implemented but in this case, the unsaturated alcohol having the formula (2) will preferably be the major positional isomer, typically in a proportion of at least 50% by weight, relative to the total weight of the positional isomers of the unsaturated alcohol.

It should be noted that the cis/trans isomers of the unsaturated alcohol may be in equilibrium in the reaction medium during the method of the invention.

The unsaturated alcohol implemented in the method of the invention may be a mixture of at least two different unsaturated alcohols. Within the meaning of the present invention, two compounds are the said to be "different" if they do not have the same empirical formula. By way of example, two cis/trans isomers or two positional isomers are not different compounds within the meaning of the present invention. Two positional isomers differ in the position of the carbon-carbon double bond on the hydrocarbon chain.

If the method makes use of a mixture of at least two different unsaturated alcohols, the said mixture preferably comprises at least 70% by weight, more preferably at least 80% by weight, advantageously at least 85% by weight, of a same given alcohol and/or of the isomer thereof (cis/trans isomer or positional isomer), relative to the total weight of the mixture of at least two different unsaturated alcohols.

Typically, the unsaturated alcohol is added via a composition of alcohols comprising at least 70% by weight of the same given unsaturated alcohol and/or of the isomers thereof (including cis/trans isomers and positional isomers), preferably at least 75% by weight of the same given unsaturated alcohol and/or of the isomers thereof, more preferably at least 80% by weight of the same given unsaturated alcohol and/or of the isomers thereof, relative to the total weight of the composition of alcohols.

According to one embodiment, the unsaturated alcohol is selected from oleic alcohol and/or its trans isomer, 10-undecenol; preferably, the unsaturated alcohol is oleic alcohol and/or its trans isomer, it being understood that, according to this embodiment, the oleic alcohol may be used via a composition of alcohols comprising at least 70% by weight of oleic alcohol and/or the isomers thereof (including cis/trans isomers and positional isomers of oleic alcohol), preferably at least 75% by weight of oleic alcohol and/or the isomers thereof, more preferably at least 80% by weight of oleic alcohol and/or the isomers thereof, relative to the total weight of the composition of alcohols.

Depending on whether the unsaturated compound is derived from natural or synthetic sources, the said unsaturated alcohol may be in its cis form and/or in its trans form when it is used in implementing the method of the invention.

According to one other embodiment, the unsaturated compound that is reacted with a saturated fatty acid according to the method of the invention is implemented with an ester of the unsaturated alcohol as defined above. In this case, the method of the invention may optionally include a preliminary step of forming the unsaturated ester, by esterification of the unsaturated alcohol as defined above.

The unsaturated ester that may be implemented as a reactant is preferably an ester of at least one unsaturated alcohol as defined above and of at least one saturated fatty acid containing from 4 to 18 carbon atoms. According to one embodiment, the fatty acid used for the esterification of the unsaturated alcohol contains from 4 to 16 carbon atoms, preferably from 4 to 12 carbon atoms.

Preferably, the unsaturated ester used as reactant in implementing the method of the invention does not comprise any functional group other than the ester functional group and the carbon-carbon double bond.

According to one embodiment, the saturated fatty acid optionally used to esterify the unsaturated alcohol replies to the formula (3):

[Chem 3]

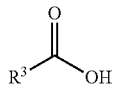

in which $R^3$ represents a monovalent alkyl radical, either linear or branched, containing from 1 to 17 carbon atoms, preferably a linear or branched alkyl containing from 3 to 15 carbon atoms, advantageously a branched alkyl containing from 5 to 11 carbon atoms.

According to one embodiment of the invention, the unsaturated ester used in implementing the invention is an ester of at least one linear, unsaturated, primary alcohol containing from 11 to 18 carbon atoms, and of at least one branched saturated fatty acid containing from 4 to 11 carbon atoms.

According to one embodiment of the invention, the unsaturated ester used in implementing the invention is an ester of at least one linear, unsaturated, primary alcohol containing from 14 to 18 carbon atoms, and of at least one branched saturated fatty acid containing from 4 to 11 carbon atoms.

The unsaturated ester used in implementing the method of the invention may be a mixture of at least two different unsaturated esters.

If the method makes use of a mixture of at least two different unsaturated esters, the said mixture preferably comprises at least 70% by weight, more preferably at least 80% by weight, advantageously at least 85% by weight, of a same given ester and/or of the isomer thereof, relative to the total weight of the mixture of at least two different unsaturated esters.

If the method makes use of an unsaturated alcohol ester, the unsaturated alcohol may be esterified beforehand according to any esterification method that is well known to the person skilled in the art.

In this case, the esterification catalyst may be identical to or different from the acid catalyst implemented for the reaction of the unsaturated compound and the fatty acid for the formation of the diesters.

The unsaturated ester can thus be represented by the formula (4) when it is obtained by reacting an unsaturated alcohol having the formula (2) with a saturated acid having the formula (3), as defined above:

[Chem 4]

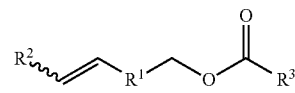

in which $R^1$, $R^2$ and $R^3$ have the same definitions as above for the formulas (2) and (3).

The cis/trans isomers of this compound having the formula (4) may be implemented during the diester formation reaction. Positional isomers may also be implemented but in this case, the unsaturated compound having the formula (4) will preferably be the major positional isomer, typically in a proportion of at least 50% by weight, relative to the total weight of the positional isomers.

The unsaturated compound, preferably in the form of an unsaturated alcohol, used as reactant in implementing the method of the invention may be derived from a synthetic or natural source, preferably a natural source, such as a plant or animal source. The fatty acid optionally used to esterify the unsaturated alcohol may also be derived from a natural source.

According to one embodiment, the unsaturated alcohol or the ester thereof used as reactant in implementing the method of the invention is derived from plant or animal oils. These may be triglycerides and other esters of the following oils: sunflower, castor, soybean and rapeseed, including hybrids or genetically modified species thereof. The oil may be treated, for example hydrocracked, in order to obtain the desired chain lengths.

Such unsaturated alcohols are commercially available.

In one particularly preferred embodiment, the unsaturated compounds used in implementing the method comprise at least one monounsaturated primary alcohol; preferably the monounsaturated primary alcohols represent at least 70% by weight, more preferably at least 80% by weight, or even at least 85% by weight, of the total weight of the unsaturated compounds, preferably unsaturated alcohols, used as reactant in implementing the method.

Saturated Fatty Acid

The method of the invention makes use of at least one saturated fatty acid containing from 2 to 18 carbon atoms, as a reactant in order to induce reaction on the carbon-carbon double bond of the unsaturated compound so as to form the diesters.

It should be noted that the saturated fatty acid that is caused to be reacted for the addition reaction on the unsaturated compound may be identical to or different from the saturated fatty acid used to esterify the unsaturated alcohol.

Thus, when the unsaturated compound is an unsaturated alcohol, and it is brought into contact with a saturated fatty acid, the esterification reaction causing esterification of the unsaturated alcohol will generally be carried out first and the addition reaction on the carbon-carbon double bond will generally be carried out subsequent thereto, since the alcohol functional group is generally more reactive than the carbon-carbon double bond.

According to one embodiment of the invention, the saturated fatty acid is a monosaturated fatty acid, containing from 4 to 17 carbon atoms, more preferably from 6 to 16 carbon atoms, advantageously from 7 to 12 carbon atoms.

According to one embodiment, the saturated fatty acid for the addition reaction according to the method corresponds to the formula (5):

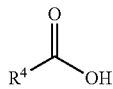

[Chem 5]

in which $R^4$ represents a monovalent alkyl radical, either linear or branched, containing from 1 to 17 carbon atoms, preferably a linear or branched alkyl containing from 6 to 16 carbon atoms, and advantageously a linear alkyl containing from 5 to 15 carbon atoms, or even from 6 to 11 carbon atoms.

The saturated fatty acid for the addition reaction according to the invention may be a fatty acid that is linear or branched, preferably linear.

Preferably, the saturated fatty acid for the addition reaction according to the invention contains from 7 to 12 carbon atoms. This chain length makes it possible to further optimise the cold properties of the composition of diesters resulting from the method.

According to one particular embodiment, when the unsaturated alcohol used in implementing the invention contains from 11 to 14 carbon atoms, preferably the saturated fatty acid used will contain from 9 to 18 carbon atoms, preferably from 9 to 14 carbon atoms, or even from 10 to 12 carbon atoms.

According to one embodiment, the saturated fatty acid implemented for the addition reaction according to the invention is selected from among octanoic acid, nonanoic acid, decanoic acid, undecanoic acid, lauric acid and mixtures thereof.

The method according to the invention may implement a single saturated fatty acid or a mixture of a plurality of saturated fatty acids. Preferably, the method according to the invention uses a single saturated fatty acid for the addition reaction according to the invention.

It is also possible to envisage implementing a mixture of at least two different saturated fatty acids. The proportions may be adjusted according to the desired properties being sought for the composition of diesters.

The saturated fatty acid is widely available commercially and may be derived from a synthetic or natural source, preferably a natural source.

Implementation of the Method

The method according to the invention comprises at least reacting the unsaturated alcohol and/or the ester thereof with the saturated fatty acid. The method typically results in an addition reaction causing addition of the acid functional group of the saturated fatty acid on the carbon-carbon double bond of the unsaturated compound in order to form at least one diester.

When the method according to the invention implements unsaturated alcohols as reactant, generally the fatty acid will react first on the alcohol functional group in order to esterify the fatty alcohol, and thereafter the fatty acid will react on the carbon-carbon double bond of the ester thus formed, in order to obtain the diesters.

When the method according to the invention implements unsaturated alcohol esters as reactant, the fatty acid will react (directly) on the carbon-carbon double bond of the ester for an addition reaction in order to obtain the diesters.

The method of the invention may be implemented in one or more steps, in particular in one or two steps. When the unsaturated compound is an ester of the unsaturated alcohol, then the method will preferably be implemented in one single step. When the unsaturated compound is an unsaturated alcohol, depending on the composition of diesters that is desired, preference may be given to a one- or two-step method, by adding one or more saturated fatty acids that may be identical or different, with or without an intermediate isolation step for isolating the formed products.

The addition reaction causing addition of the saturated fatty acid to the unsaturated compound, according to the invention, is carried out in the presence of one or more acid catalyst(s). The catalyst may be selected from among all known catalysts for the addition reaction for adding an acid functional group across a carbon-carbon double bond. According to one embodiment, the acid catalyst is selected from among:

perchloric acid, a catalyst comprising a sulphonic acid functional group or sulphonate functional group, typically having the formula (6), optionally supported,

[Chem 6]

or the sulphonate form thereof, where R is a hydrogen atom or a linear, branched or cyclic hydrocarbon radical having from 1 to 18 carbon atoms, optionally substituted by one or more heteroatoms, for example of a type such as nitrogen, fluorine, oxygen, sulfur or silicon;

triflates (trifluoromethylsulfonate), typically having the formula $CF_3SO_3^-M^+$, where M represents a metal selected from among bismuth, copper, silver and iron.

According to one embodiment, in the formula $RSO_3H$ above, R represents a hydrogen atom, or a linear or branched alkyl or alkenyl radical, a cycloalkyl radical, the said radicals preferably having from 1 to 12 carbon atoms, the said radicals being optionally substituted by one or more fluorine atoms and/or oxygen atoms. This catalyst may optionally be supported on silica.

The catalysts that may possibly be implemented in the invention may be commercially available.

The catalyst used in implementing the invention may be a homogeneous catalyst or a heterogeneous catalyst.

When the catalyst is a heterogeneous catalyst, it may be supported on a material which may be selected from among alumina, silica, etc. By way of non-limiting example, mention may be made of triflic acid supported on silica.

According to one embodiment, the method of the invention optionally includes a separation step for separating the catalyst from the composition of diesters thus obtained.

When the method is carried out in two steps, including an esterification reaction and an addition reaction, the acid catalyst implemented for the addition reaction of the fatty acid on the carbon-carbon double bond, may be identical to or different from the catalyst used for the esterification reaction causing esterification of the unsaturated alcohol.

According to one embodiment of the invention, the method implements a single catalyst, which will serve to enable the esterification reaction causing esterification of the unsaturated alcohol and the addition reaction causing addition of the saturated fatty acid on the carbon-carbon double bond of the unsaturated compound. Preferably, the esterification and addition reactions are carried out in the presence of the same given catalyst. In this case, the said catalyst will preferably be selected from among triflic acid, optionally supported, and triflates.

When the method is implemented in two steps in batch mode, then the first step is an esterification reaction which may be implemented under conditions well known to the person skilled in the art, with for example a catalyst of the type such as para toluene sulphonic acid (PTSA).

The method according to the invention may optionally include intermediate steps and/or subsequent washing and/or purification steps.

The method according to the invention may be implemented in one step with a batch introduction mode, or in two steps with a sequential introduction mode, or in two steps with a batch introduction mode.

Within the meaning of the present invention, the allusion to 'implementation in one-step with a batch introduction mode' is understood to refer to a method comprising a single compound introduction step for introducing the entirety of the unsaturated compound and the entirety of the saturated fatty acids, in order to obtain the diesters. In the event of the unsaturated compound being an unsaturated alcohol ester, this embodiment will be preferred. In the event of the unsaturated compound being an unsaturated alcohol and the saturated fatty acids that enable the addition reaction and the esterification reaction being identical, this embodiment may thus then be preferred. This embodiment could also be envisaged when the method involves deploying an unsaturated alcohol and various different saturated fatty acids, if a statistical distribution of diesters is desired.

Within the meaning of the present invention, the allusion to 'implementation in two steps with a sequential introduction mode' is understood to refer to a method comprising a first introduction step for introducing the unsaturated compound and a portion of the saturated fatty acids in order to carry out a first reaction, followed thereafter by a second introduction step for introducing the other portion of the saturated fatty acids in order to carry out a second reaction, without an intermediate isolation step for isolating the compounds obtained at the end of the first reaction, prior to adding of the other portion of the saturated fatty acids for the second reaction. Typically, according to this embodiment, the unsaturated compound is an unsaturated alcohol (and not the ester thereof) and the method makes use of two different saturated fatty acids, a first fatty acid for the first reaction and a second fatty acid for the second reaction. Generally, the first reaction will be an esterification reaction and the second reaction will be an addition reaction on the olefinic double bond of the unsaturated alcohol. In order to obtain greater selectivity towards a specific diester, it may be preferable to implement the method of the invention in a sequential manner. This embodiment may be envisaged in the event it is sought to react different fatty acids with the unsaturated alcohol, that is, with one specific fatty acid for the esterification reaction and another specific fatty acid for the addition reaction.

Within the meaning of the present invention, the allusion to 'implementation in two steps with a batch introduction mode' is understood to refer to a method comprising a first introduction step for introducing the unsaturated compound and a portion of the saturated fatty acids in order to carry out a first reaction, typically the esterification reaction, followed thereafter by a second introduction step for introducing the other portion of the saturated fatty acids in order to carry out a second reaction, typically the addition reaction, with at least one intermediate isolation step for isolating the compounds obtained at the end of the first reaction, prior to adding the other portion of the saturated fatty acids for the second reaction. Typically, according to this embodiment, the unsaturated compound is an unsaturated alcohol (and not the ester thereof) and the method makes use of two different saturated fatty acids, a first fatty acid for the first reaction and a second fatty acid for the second reaction. Generally, the first reaction will be an esterification reaction and the second reaction will be an addition reaction across the olefinic double bond of the unsaturated alcohol.

For example, when the method of the invention is implemented in two steps with a batch introduction mode, that include a first esterification reaction and a second addition reaction, the method may then include one or more intermediate steps of washing and/or purification. These intermediate steps provide the means to separate any potential by-products that may be formed and/or the reactants that remain unreacted.

On the contrary, when the method of the invention is implemented in one step with a batch introduction mode or in two steps with a sequential introduction mode based on an unsaturated alcohol, the method of the invention typically will not include any intermediate washing and/or purification steps, but the method may include water withdrawal operations (implemented for example during the ester formation step) for withdrawing the water formed during the esterification reaction. The device may comprise a water withdrawal system.

Whether these be during batch or sequential implementation, in one or more steps, the method of the invention may optionally include subsequent washing and/or purification steps that provide the means to separate any potential by-products that may be formed and/or the reactants that remain unreacted.

In order to obtain a better yield, it would be preferable to avoid the intermediate treatment/processing steps, and therefore implementation in one single batch step or in two sequential steps would be preferred.

When the acid catalyst is liable to deteriorate in the presence of water, as in the case of triflic acid, it would be preferable to carry out the esterification reaction causing esterification of the unsaturated alcohol under vacuum or with withdrawal of the water formed.

Preferably, the method according to the invention does not include a subsequent hydrogenation step of hydrogenating the composition of diesters obtained at the end of the method.

The method of the invention makes it possible in particular to obtain, at the end of the reaction between the unsaturated compound and the saturated fatty acid, a composition of esters comprising predominantly diesters, in particular, the resulting ester composition obtained at the end of the method of the invention typically comprises at least 60% by weight, advantageously at least 70% by weight of diesters, relative to the total weight of the composition resulting from the method.

According to one embodiment, the method comprises a subsequent reactant separation step for separating the reactants or the monoesters of unsaturated alcohols from the composition resulting from the method, for example by stripping (vacuum distillation).

The composition of diesters obtained after purification (ie separation of the reactants or monoesters of unsaturated alcohols) may for example comprise at least 80% by weight, or even at least 90% by weight of diesters, relative to the total weight of the composition of diesters obtained after purification.

According to one embodiment of the invention, the addition reaction between the unsaturated alcohol ester and the saturated fatty acid is carried out at a temperature ranging from 20 to 120° C., preferably ranging from 30 to 100° C., advantageously ranging from 40 to 90° C.

When the method is implemented in one single batch step, preferably with an unsaturated compound of unsaturated alcohol ester type, the method is preferably implemented:
  at a temperature ranging from 20° C. to 130° C., preferably from 30 to 120° C., more preferably from 40 to 110° C.; and/or
  at atmospheric pressure or under vacuum.

Preferably, when the method is implemented in one single batch step, preferably with an unsaturated compound of unsaturated alcohol ester type, the method is preferably implemented at a temperature ranging from 40 to 110° C. and at atmospheric pressure.

When the method is implemented in two steps (in batch or sequential mode), starting from an unsaturated compound of a type such as unsaturated alcohol, the method typically comprises:
  a) A first esterification reaction at a temperature preferably ranging from 60 to 150° C., preferably from 65 to 130° C., more preferably from 80 to 110° C.; and/or at atmospheric pressure or under vacuum, preferably under vacuum; and
  b) A second addition reaction causing addition of fatty acid on the unsaturated alcohol ester at a temperature preferably ranging from 20° C. to 130° C., preferably from 30 to 120° C., more preferably from 40 to 110° C.; and/or at atmospheric pressure or under vacuum, preferably at atmospheric pressure.

When the method is implemented in two steps, in batch or sequential mode, it is also possible to envisage using two different catalysts, a first catalyst for the first reaction and a second catalyst for the second reaction.

According to one embodiment, the addition reaction causing addition of the saturated fatty acid to the unsaturated compound in the presence of the acid catalyst is carried out in accordance with one or more of the following conditions:
  a molar ratio of the unsaturated compound/saturated fatty acid ranging from 1/10 to 1/1, preferably from 1/8 to 1/2, more preferably ranging from 1/7 to 1/3; and/or
  a molar ratio of the unsaturated compound/catalyst ranging from 1/0.05 to 1/1, preferably from 1/0.1 to 1/0.8, more preferably from 1/0.2 to 1/0.5.

When the reaction is implemented in two steps, in batch or sequential mode, the first step of esterification is implemented under conventional conditions that are well known to the person skilled in the art, for example, with a slight excess of the saturated fatty acid, typically with a molar ratio of unsaturated alcohol to saturated fatty acid ranging from 1/10 to 1/1.01, or even from 1/5 to 1.04 or from 1/2 to 1/1.05. The catalyst for the esterification reaction may be any well-known catalyst deemed suitable for carrying out an esterification step. For example, the esterification catalyst may be para toluene sulphonic acid (PTSA).

The progression of the reaction may be monitored by gas chromatography coupled with a flame ionisation detector (GC-FID), according to methods known to the person skilled in the art.

Within the meaning of the present invention, the term 'conversion' refers to the quantity expressed in percentage by weight of the unsaturated compound(s) that has(have) reacted and the term 'selectivity' refers to the quantity expressed in percentage by weight of a specific targeted diester relative to the total weight of the diesters formed.

The diesters that may be obtained at the end of the method generally comprise at least one compound having the formula (1):

[Chem 1]

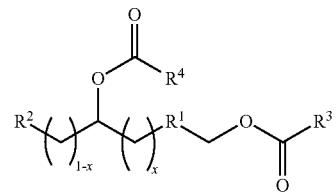

wherein:
$R^1$ is a linear or branched alkylene or alkenylene radical containing from 3 to 15 carbon atoms, preferably a linear or branched alkylene radical containing from 3 to 15 carbon atoms, more preferably a linear alkylene radical containing from 5 to 12 carbon atoms;
$R^2$ is a hydrogen atom or a linear or branched alkyl or alkenyl radical containing from 1 to 16 carbon atoms, preferably a hydrogen atom or a linear or branched alkyl radical containing from 2 to 12 carbon atoms, more preferably a hydrogen atom or a linear or branched alkyl radical containing from 4 to 10 carbon atoms;
it being understood that the sum of the carbon atoms of the radicals $R^1$ and $R^2$ ranges from 8 to 17 carbon atoms, preferably from 8 to 16 carbon atoms, more preferably from 11 to 16 carbon atoms;
$R^3$ and $R^4$ are, independently of each other, a linear or branched monovalent alkyl radical containing from 3 to 17 carbon atoms, preferably a linear or branched alkyl radical containing from 3 to 15 carbon atoms, or from 3 to 13 carbon atoms;
x is an integer equal to 0 or 1.

The composition of diesters obtained at the end of the method will typically comprise one or more compounds having the formula (1), in particular with compounds where x is equal to zero, and compounds where x is equal to 1; however, the composition of diesters obtained at the end of the method may also comprise one or more positional isomers of the compound having the formula (1), in which the group —OCOR4 will be connected to a carbon atom other than one of the two carbon atoms of the carbon-carbon double bond of the unsaturated compound, the reactant in the addition reaction. Indeed, as indicated above, positional isomers of the unsaturated compound may be formed, ie isomers where the carbon-carbon double bond has changed position on the hydrocarbon chain of the unsaturated compound, before the addition reaction according to the invention.

In the formula (1), when R2 is a hydrogen atom, then preferably x is equal to 0. In this embodiment, the composition of diesters obtained at the end of the method will typically comprise compounds having the formula (1) where x is equal to zero; however, the composition of diesters obtained at the end of the method may also comprise one or more positional isomers of the compound having the formula (1), in which the group —OCOR4 will be connected to a carbon atom other than one of the two carbon atoms of the carbon-carbon double bond of the starting unsaturated alcohol. Indeed, as indicated above, positional isomers of the unsaturated compound may be formed, ie isomers where the carbon-carbon double bond has changed position on the hydrocarbon chain of the unsaturated compound, before the addition reaction according to the invention.

The invention also relates to a composition of diesters as such, comprising at least one compound replying to the formula (1) defined in the present invention.

The compound having the formula (1) may be obtained by reacting an unsaturated alcohol having the formula (2) or an unsaturated alcohol ester having the formula (4) with a saturated fatty acid having the formula (5).

When the method is implemented in one single batch step starting from an unsaturated alcohol having the formula (2) with saturated acids having the formula (3) and saturated acids having the formula (5), then typically, the composition of diesters according to the invention will comprise a mixture of compounds having the formula (1), compounds having the formula (7), compounds having the formula (8), and compounds having the formula (9). Quite obviously, if the acids having the formula (3) and the acids having the formula (5) are identical, then all of these diesters will be identical.

When the method is implemented in sequential mode (or in two batch steps), starting from an unsaturated alcohol having the formula (2) with saturated acids having the formula (3) and saturated acids having the formula (5), then typically, the composition of diesters according to the invention will comprise at least one diester having the formula (1), and possibly diesters having the formula (7); and/or possibly diesters having the formula (8), and/or possibly diesters having the formula (9).

The formulas (7), (8) and (9) are the following formulas:

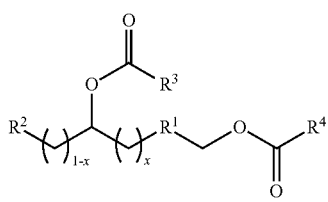

[Chem 7]

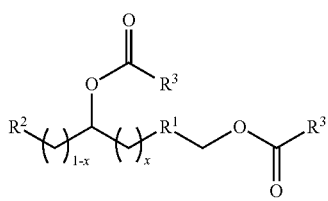

[Chem 8]

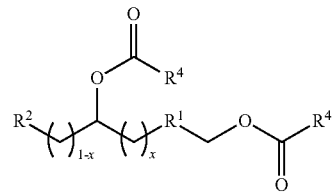

[Chem 9]

In which, R1, R2, R3, and R4, and x have the same definitions as in the formula (1).

When it is sought to obtain specific diesters having the formula (1) in which R3 and R4 are different, it would be preferable to make use of different fatty acids, for the esterification of the unsaturated alcohol and for the addition reaction on the carbon-carbon double bond of the unsaturated compound; and it would be preferable to implement the method in one step starting from the unsaturated alcohol ester, or in two batch or sequential steps starting from the unsaturated alcohol, by performing firstly, the esterification of the unsaturated alcohol with a first acid, and then the addition reaction causing addition of a second acid on the carbon-carbon double bond of the unsaturated ester thus obtained.

According to one embodiment where the saturated fatty acid implemented for the addition reaction is other than the saturated fatty acid of the acid part of the unsaturated ester, the composition of diesters obtained at the end of the method comprises at least diesters having the formula (1) and at least diesters having the formula (9).

Preferably, the composition of diesters obtained at the end of the method comprises:
  from 40 to 99% by weight of diesters having the formula (1) and the positional isomers thereof, preferably from 50 to 95% by weight of diesters having the formula (1) and the positional isomers thereof, more preferably from 60 to 90% by weight of diesters having the formula (1) and the positional isomers thereof; and
  from 1 to 60% by weight of diesters having the formula (9) and the positional isomers thereof, preferably from 5 to 50% by weight of diesters having the formula (9) and the positional isomers thereof, more preferably from 10 to 40% by weight of diesters having the formula (9) and the positional isomers thereof,
  relative to the total weight of the composition of diesters.

In the formulas (1) and (7), as also in the formulas (8) and (9), preferably the radicals are such that:
  $R^1$ is a linear or branched alkylene radical containing from 3 to 15 carbon atoms, more preferably a linear alkylene radical containing from 5 to 12 carbon atoms;
  $R^2$ is a hydrogen atom or a linear or branched alkyl radical containing from 4 to 10 carbon atoms;
  it being understood that the sum of the carbon atoms of the radicals $R^1$ and $R^2$ ranges from 8 to 16 carbon atoms, more preferably from 11 to 16 carbon atoms;
  $R^3$ is a monovalent alkyl radical, either linear or branched, preferably branched, containing from 3 to 9 carbon atoms, preferably from 4 to 8 carbon atoms;
  $R^4$ is a monovalent alkyl radical, either linear or branched, preferably linear, containing from 3 to 17 carbon atoms, preferably from 3 to 15 carbon atoms.

In one embodiment where the method uses in implementation a saturated fatty acid having the formula (3) where $R^3$ is a branched monovalent alkyl radical, and a saturated fatty acid having the formula (5) where $R^4$ is a linear monovalent alkyl radical, the composition of diesters obtained will comprise predominantly a diester having the formula (1) as compared to the diesters having the formula (1), (7), (8) and (9). In particular, after any eventual final purification, the composition of diesters will typically comprise at least 50% by weight of the diester having the formula (1), preferably at least 55% by weight of the diester having the formula (1), preferably at least 60% by weight of the diester having the formula (1), relative to the total weight of the composition of diesters.

A compound will be said to be predominantly present relative to another compound in a composition if it is present in a mass proportion that is higher than that of the other compound in the said composition.

In one embodiment where the method implements a saturated fatty acid having the formula (3) where $R^3$ is a branched monovalent alkyl radical, and a saturated fatty acid having the formula (5) where $R^4$ is a linear monovalent alkyl radical, and where the method is implemented in two steps (batch or sequential), the composition of diesters obtained will predominantly comprise a diester having the formula (1) as compared to the diesters having the formula (1), (7), (8) and (9). In particular, after any eventual final purification, the composition of diesters will typically comprise at least 65% by weight of the diester having the formula (1), preferably at least 70% by weight of the diester having the formula (1), more preferably at least 75% by weight of the diester having the formula (1), relative to the total weight of the composition of diesters.

The composition of diesters obtained at the end of the method may also comprise by-products (also known as "secondary products"), for example monoesters of unsaturated alcohols.

It should be noted that the starting unsaturated compound may comprise positional isomers of the unsaturated compounds illustrated by the formula (2) or the formula (4) above. Therefore, the composition of diesters obtained may also further comprise positional isomers of the compounds illustrated by the formula (1).

The composition of diesters obtained at the end of the method advantageously has a kinematic viscosity at 40° C. ranging from 5 to 100 mm²/s, preferably from 6 to 50 mm²/s, more preferably from 7 to 40 mm²/s, measured for example according to the standard ASTM D7042.

The composition of diesters obtained at the end of the method advantageously has a kinematic viscosity at 100° C. ranging from 1 to 20 mm²/s, preferably from 2 to 15 mm²/s, more preferably from 2 to 10 mm²/s, measured for example according to the ASTM D7042 standard.

Composition of Diesters

The object of the present invention also relates to a composition of diesters that is obtainable by the method of the invention.

The composition of diesters according to the invention typically comprises at least one compound having the formula (1):

[Chem 1]

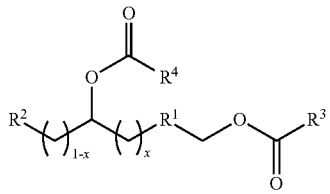

in which:
$R^1$ is a linear or branched alkylene or alkenylene radical containing from 3 to 15 carbon atoms, preferably a linear or branched alkylene radical containing from 3 to 15 carbon atoms, more preferably a linear alkylene radical containing from 5 to 12 carbon atoms;

$R^2$ is a hydrogen atom or a linear or branched alkyl or alkenyl radical containing from 1 to 16 carbon atoms, preferably a hydrogen atom or a linear or branched alkyl radical containing from 2 to 12 carbon atoms, more preferably a hydrogen atom or a linear or branched alkyl radical containing from 4 to 10 carbon atoms;

it being understood that the sum of the carbon atoms of the radicals $R^1$ and $R^2$ ranges from 8 to 17 carbon atoms, preferably from 8 to 16 carbon atoms, more preferably from 11 to 16 carbon atoms;

$R^3$ and $R^4$ are, independently of each other, a linear or branched monovalent alkyl radical containing from 3 to 17 carbon atoms, preferably a linear or branched alkyl radical containing from 3 to 15 carbon atoms;

x is an integer equal to 0 or 1.

The composition of diesters according to the invention will typically comprise one or more compounds having the formula (1), in particular with compounds where x is equal to zero and compounds where x is equal to 1; however, the composition of diesters according to the invention may also comprise one or more positional isomers of the compound having the formula (1), in which the group —OCOR4 will be connected to a carbon atom other than one of the two carbon atoms of the carbon-carbon double bond of the unsaturated compound, the reactant in the addition reaction. Indeed, as indicated above, positional isomers of the unsaturated compound may be formed, ie isomers where the carbon-carbon double bond has changed position on the hydrocarbon chain of the unsaturated compound, before the addition reaction according to the invention.

In the formula (1), when R2 is a hydrogen atom, then preferably x is equal to 0. In this embodiment, the composition of diesters according to the invention will typically comprise compounds having the formula (1) where x is equal to zero; however, the composition of diesters according to the invention may also comprise one or more positional isomers of the compound having the formula (1), in which the group —OCOR4 will be connected to a carbon atom other than one of the two carbon atoms of the carbon-carbon double bond of the starting unsaturated alcohol. Indeed, as indicated above, positional isomers of the unsaturated compound may be formed, ie isomers where the carbon-carbon double bond has changed position on the hydrocarbon chain of the unsaturated compound, before the addition reaction according to the invention.

The composition of diesters according to the invention may also comprise a mixture of at least two diesters:
one or more diesters having the formula (1) and the positional isomers thereof; and
one or more diesters having the formula (9) and the positional isomers thereof;
it being understood that according to this embodiment, $R^3$ is different from $R^4$.

According to this embodiment, the composition of diesters preferably comprises a mass ratio of diester having the formula (1)/diester having the formula (9) ranging from 10/90 to 90/10, preferably from 20/80 to 80/20.

According to one embodiment, the composition of diesters according to the invention comprises:

from 40 to 99% by weight of diesters having the formula (1) and the positional isomers thereof, preferably from 50 to 95% by weight of diesters having the formula (1) and the positional isomers thereof, more preferably from 60 to 90% by weight of diesters having the formula (1) and the positional isomers thereof; and from 1 to 60% by weight of diesters having the formula (9) and the positional isomers thereof, preferably from 5 to 50% by weight of diesters having the formula (9) and the positional isomers thereof, more preferably from 10 to 40% by weight of diesters having the formula (9) and the positional isomers thereof;

relative to the total weight of the composition of diesters.

The invention also relates to the diesters, as such, having the formula (1) defined in the present invention.

According to one embodiment, in the formula (1):

$R^1$ is a linear or branched alkylene or alkenylene radical containing from 3 to 15 carbon atoms, more preferably a linear alkylene radical containing from 5 to 12 carbon atoms;

$R^2$ is a hydrogen atom or a linear or branched alkyl radical containing from 2 to 12 carbon atoms, more preferably a hydrogen atom or a linear or branched alkyl radical containing from 4 to 10 carbon atoms;

it being understood that the sum of the carbon atoms of the radicals $R^1$ and $R^2$ ranges from 8 to 16 carbon atoms, more preferably from 11 to 16 carbon atoms;

$R^3$ is a linear or branched monovalent alkyl radical containing from 3 to 9 carbon atoms, advantageously a branched alkyl containing from 4 to 8 carbon atoms;

$R^4$ is a linear or branched monovalent alkyl radical containing from 3 to 17 carbon atoms, advantageously a linear alkyl containing from 3 to 15 carbon atoms;

x is a integer equal to 0 o u 1.

In the formulas (1) and (9), as also in the formulas (7) and (8), preferably, the radicals are such that:

$R^1$ is a linear or branched alkylene radical containing from 3 to 15 carbon atoms, more preferably a linear alkylene radical containing from 5 to 12 carbon atoms;

$R^2$ is a hydrogen atom or a linear or branched alkyl radical containing from 4 to 10 carbon atoms;

it being understood that the sum of the carbon atoms of the radicals $R^1$ and $R^2$ ranges from 8 to 16 carbon atoms, more preferably from 11 to 16 carbon atoms;

$R^3$ is a monovalent alkyl radical, either linear or branched, preferably branched, containing from 3 to 9 carbon atoms, preferably from 4 to 8 carbon atoms;

$R^4$ is a monovalent alkyl radical, either linear or branched, preferably linear, containing from 3 to 17 carbon atoms, preferably from 3 to 15 carbon atoms.

The composition of diesters according to the invention typically comprises at least 70% by weight, preferably at least 75% by weight, more preferably at least 80% by weight of compounds corresponding to the formula (1) defined in the present invention, relative to the total weight of the composition of diesters.

According to one other embodiment, the composition of diesters according to the invention comprises diesters having the formula (1) and diesters having the formula (9) in a combined amount of at least 70% by weight, preferably at least 75% by weight, more preferably at least 80% by weight, relative to the total weight of the composition of diesters. Depending on the applications envisaged, it may be preferable to have a mixture of two diesters obtained by making use of two different saturated fatty acids.

According to these two embodiments, preferably, in the formula (1) and where appropriate in the formula (9), the radical $R^3$ is a branched radical and the radical $R^4$ is a linear radical.

Uses

The method according to the invention makes it possible to obtain a composition of diesters with good conversion rate and providing the means to obtain a specific diester with high selectivity.

The diester composition may be used in a lubricating composition as the sole base oil, but advantageously in combination with some other base oil. The term "other base oil" should be understood to refer to a base oil other than diesters.

The lubricating composition comprising the composition of diesters according to the invention may be used to lubricate the various parts of a vehicle, in particular the various parts of an engine or transmission of a vehicle, or the various parts of a marine engine or of industrial machinery engine, for example for civil engineering.

The composition of diesters may also be used in a cosmetic or pharmaceutical composition as an emollient, either alone or in combination with some other fatty substance. The term "other fatty substance" should be understood to refer to a fatty substance other than the diesters according to the invention.

The cosmetic or pharmaceutical composition comprising the composition of diesters according to the invention may be used for topical application, typically on the skin, the nails, the lips, the hair, and the scalp.

The object of the invention also relates to the cosmetic or pharmaceutical use of the composition of diesters according to the invention as: a skincare product (serums, creams, balms, etc), a hygiene product, a sunscreen/after-sun care product, a make-up product, a make-up remover, a perfumed product, an antiperspirant product.

Additionally the object of the invention also relates to a cosmetic or pharmaceutical treatment method for treating the skin, nails, lips, hair or scalp, that comprises at least one application step of applying to the skin, nails, lips, hair or the scalp, a composition of diesters according to the invention.

Finally, the invention also covers a cosmetic treatment method comprising at least one application step of applying, preferably by spreading, over the skin, the nails, the lips, the hair or the scalp, the composition of diesters according to the invention.

Lubricating Composition

The object of the invention also relates to a lubricating composition comprising the composition of diesters according to the invention and at least one additive and/or at least one other base oil.

These other base oils may be selected from the base oils conventionally used in the field of lubricating oils, such as mineral, synthetic or natural, animal or plant oils, or mixtures thereof.

The other base oils of the lubricating compositions according to the invention may in particular be oils of mineral or synthetic origin belonging to groups I to V according to the classes as defined in the API classification (or the equivalents thereof according to the Technical Association of the European Lubricants Industry, ATIEL classification) and presented in Table 1 below, or mixtures thereof.

TABLE 1

| | Saturates Content (by weight) | Sulfur Content (by weight) | Viscosity Index (VI) |
|---|---|---|---|
| Group I Mineral Oils | <90% | >0.03% | 80 ≤ VI < 120 |
| Group II Hydrocracked Oils | ≥90% | ≤0.03% | 80 ≤ VI < 120 |
| Group III Hydrocracked or Hydro-Isomerised Oils | ≥90% | ≤0.03% | ≥120 |
| Group IV | Polyalphaolefins (PAO) | | |
| Group V | Esters and other bases not included in groups I to IV | | |

The other mineral-based oils include all types of base oils obtained by atmospheric and vacuum distillation of crude oil, followed by refining operations such as solvent extraction, deasphalting, solvent dewaxing, hydrotreating, hydrocracking, hydroisomerisation and hydrofinishing.

Blends of synthetic and mineral oils, which may be biosourced, may also be used.

The other base oils of the lubricating compositions according to the invention may also be selected from synthetic oils, such as certain esters of carboxylic acids and alcohols, polyalphaolefins (PAO), and polyalkylene glycol (PAG) obtained by polymerisation or copolymerisation of alkylene oxides containing from 2 to 8 carbon atoms, in particular from 2 to 4 carbon atoms.

The PAOs used as other base oils are for example obtained from monomers containing from 4 to 32 carbon atoms, for example from octene or decene. The weight average molecular weight (ie mass average molar mass) of PAO may vary quite widely. Preferably, the weight average molecular weight of the PAO is less than 600 Da. The weight average molecular weight of the PAO may also range from 100 to 600 Da, from 150 to 600 Da, or even from 200 to 600 Da.

Advantageously, the one or more other base oil(s) of the lubricating composition according to the invention are selected from among polyalphaolefins (PAO), polyalkylene glycols (PAG), and esters of carboxylic acids and alcohols.

According to an alternative embodiment, the one or more other base oil(s) of the lubricating composition according to the invention may be selected from the base oils of group II or III. It is up to a person skilled in the art to adjust the content level of the base oil to be used in implementation in a lubricating composition.

According to one embodiment, the lubricating composition according to the invention comprises:
from 5 to 95% by weight, preferably from 10 to 70% by weight, advantageously from 15 to 50% by weight, of the composition of diesters according to invention; and
from 5 to 95% by weight, preferably from 30 to 90% by weight, advantageously from 50 to 85% by weight, of one or more other base oil(s);
relative to the total weight of the lubricating composition according to the invention.

According to one embodiment, the one or more additive(s) of the lubricating composition are selected from among friction modifiers, detergents, anti-wear additives, extreme pressure additives, dispersants, antioxidants, pour point depressants, antifoaming agents, and mixtures thereof. These additives are well known to the person skilled in the art in the field of mechanical parts lubrication.

These additives may be introduced individually and/or in the form of a blend/mixture quite similar to those already available for sale for the formulations of commercial lubricants for vehicle engines, with a performance level as defined by the European Automobile Manufacturers' Association (ACEA) and/or the American Petroleum Institute (API), well known to the person skilled in the art.

A lubricating composition according to the invention may comprise at least one friction modifier additive. The friction modifier additive may be selected from a compound providing metal elements and an ash-free compound. Among the compounds providing metal elements, mention may be made of complexes of transition metals such as Mo, Sb, Sn, Fe, Cu, Zn, the ligands of which may be hydrocarbon compounds comprising oxygen, nitrogen, sulfur or phosphorus. The ash-free friction modifier additives are generally derived from organic sources and may be selected from among monoesters of fatty acids and polyols, alkoxylated amines, alkoxylated fatty amines, fatty epoxides, borate fatty epoxides; fatty amines, or fatty acid glycerol esters. According to the invention, the fatty compounds comprise at least one hydrocarbon group containing from 10 to 24 carbon atoms.

A lubricating composition according to the invention may comprise from 0.01 to 2% by weight, or from 0.01 to 5% by weight, preferably from 0.1 to 1.5% by weight, or from 0.1 to 2% by weight of friction modifier additive, relative to the total weight of the lubricating composition.

A lubricating composition implemented according to the invention may comprise at least one antioxidant additive.

The antioxidant additive generally provides the means to delay the degradation of the composition during use in operation. This degradation may in particular result in the formation of deposits, in the presence of sludge, or in an increase in the viscosity of the composition.

The antioxidant additives act in particular as free radical inhibitors or hydroperoxide destroyers. Among the antioxidant additives that are commonly used, mention may be made of such types as for example phenolic antioxidant additives, amine antioxidant additives, phospho-sulfur antioxidant additives. Certain of these antioxidant additives, for example phospho-sulfur antioxidant additives, may be ash generators. The phenolic antioxidant additives may be ash-free or indeed may be in the form of basic or neutral metal salts. The antioxidant additives may in particular be selected from among sterically hindered phenols, sterically hindered phenol esters, and sterically hindered phenols comprising a thioether bridge, diphenylamines, diphenylamines substituted with at least one C1-C12 alkyl group, N,N'-dialkyl-aryl-diamines and mixtures thereof.

Preferably according to the invention, the sterically hindered phenols are selected from among compounds comprising a phenol group of which at least one carbon that is vicinal to the carbon bearing the alcohol functional group is substituted by at least one C1-C10 alkyl group, preferably a C1-C6 alkyl group, preferably a C4 alkyl group, preferably by the tert-butyl group.

Amino compounds are another class of antioxidant additives that may be used, possibly in combination with the phenolic antioxidant additives. Examples of amino compounds are aromatic amines, for example aromatic amines having the formula NQ1Q2Q3 in which Q1 represents an aliphatic group or an optionally substituted aromatic group; Q2 represents an optionally substituted aromatic group; Q3 represents a hydrogen atom, an alkyl group, an aryl group, or a group having the formula Q4S(O)ZQ5 in which Q4 represents an alkylene group or an alkenylene group; Q5 represents an alkyl group, an alkenyl group, or an aryl group; and z represents 0, 1 or 2

Sulfurised alkyl phenols or the alkali and alkaline earth metal salts thereof may also be used as antioxidant additives.

Another class of antioxidant additives is the class of copper compounds, for example copper thio- or dithio-phosphates, salts of copper and of carboxylic acids, dithio-carbamates, sulphonates, phenates, copper acetylacetonates. Copper I and II salts, salts of succinic acid or succinic anhydride may also be used.

A lubricating composition according to the invention may contain all types of antioxidant additives known to the person skilled in the art.

Advantageously, a lubricating composition according to the invention comprises at least one ash-free antioxidant additive.

A lubricating composition according to the invention may comprise from 0.5 to 2% by weight of at least one antioxidant additive, relative to the total weight of the composition.

A lubricating composition according to the invention can also comprise at least one detergent additive.

Detergent additives generally provide the means to reduce the formation of deposits on the surface of metal parts by dissolving the secondary products of oxidation and combustion.

The detergent additives which may be used in a lubricating composition according to the invention are generally known to the person skilled in the art. The detergent additives may be anionic compounds comprising a long lipophilic hydrocarbon chain and a hydrophilic head. The associated cation may be a metal cation of an alkali or alkaline earth metal.

The detergent additives are preferably selected from among alkali metal salts or alkaline-earth metal salts of carboxylic acids, sulfonates, salicylates, naphthenates, as well as phenate salts. The alkali and alkaline-earth metals are preferably calcium, magnesium, sodium or barium.

These metal salts generally comprise the metal in a stoichiometric quantity or else in excess, therefore in a quantity greater than the stoichiometric quantity. These are then overbased detergent additives; the excess metal contributing the overbased character to the detergent additive is then generally in the form of an oil-insoluble metal salt, for example a carbonate, a hydroxide, an oxalate, an acetate, a glutamate, preferentially a carbonate.

A lubricating composition according to the invention may for example comprise from 2 to 4% by weight of detergent additive, relative to the total weight of the composition.

Also, a lubricating composition according to the invention may comprise at least one dispersing agent, which is separate from the compounds of such type as succinimide as defined according to the invention.

The dispersing agent may be selected from Mannich bases, succinimides, for example of such type as polyisobutylene succinimide.

A lubricating composition implemented according to the invention may for example comprise from 0.2 to 10% by weight of one or more dispersing agent(s) which is(are) separate from the compounds of such type as succinimide as defined according to the invention, relative to the total weight of the composition.

A lubricating composition according to the invention may additionally also comprise at least one anti-wear and/or extreme-pressure agent.

There are a wide variety of existing anti-wear additives. Preferably, for the lubricating composition according to the invention, the anti-wear additives are selected from among phospho-sulfur additives such as metal alkylthiophosphates, in particular zinc alkylthiophosphates, and more specifically zinc dialkyldithiophosphates or ZnDTP. The preferred compounds are those having the formula $Zn((SP(S)(OQ6)(OQ7))2$, in which Q6 and Q7, which may be identical or different, independently represent an alkyl group, preferentially an alkyl group containing from 1 to 18 carbon atoms.

Amine phosphates are also anti-wear additives which may be used in a composition according to the invention. However, the phosphorus provided by these additives may act as a poisonous substance for the catalytic systems of automobiles because these additives are ash generators. These effects may be minimised by partially substituting the amine phosphates with additives that do not provide phosphorus, such as, for example, polysulphides, in particular sulfur-containing olefins.

A lubricating composition according to the invention may comprise from 0.01 to 15% by weight, preferably from 0.1 to 10% by weight, preferentially from 1 to 5% by weight of anti-wear agent(s), relative to the total weight of the composition A lubricating composition according to the invention may further comprise at least one antifoaming agent.

The antifoaming agent may be selected from among polyacrylates and polysiloxanes.

A lubricating composition according to the invention may comprise from 0.01 to 2% by mass, or from 0.01 to 5% by mass; preferably from 0.1 to 1.5% by mass, or from 0.1 to 2% by mass of antifoaming agent; relative to the total weight of the composition.

A lubricating composition suitable for the invention may also comprise at least one pour point depressant additive, accordingly also referred to as "PPD" (for "Pour Point Depressant") agents.

By slowing down the formation of paraffin crystals, pour point depressants generally ameliorate the cold behaviour of the composition. By way of examples of pour point depressant additives, mention may be made of alkyl polymethacrylates, polyacrylates, polyarylamides, polyalkylphenols, polyalkylnaphthalenes and alkylated polystyrenes.

The lubricating composition according to the invention may comprise:
  from 5 to 94.9% by weight, preferably from 10 to 70% by weight, advantageously from 15 to 50% by weight, of the composition of diesters according to the invention; and
  from 5 to 94.9% by weight, preferably from 30 to 90% by weight, advantageously from 50 to 85% by weight, of one or more other base oil(s);
  from 0.1 to 15% by weight, preferably from 0.5 to 10% by weight, advantageously from 1 to 5% by weight of one or more additives selected from among friction modifiers, viscosity index modifiers, detergents, dispersants, anti-wear and/or extreme pressure additives, antioxidants, pour point depressants, anti-foaming agents and mixtures thereof;
  relative to the total weight of the lubricating composition according to the invention.

The lubricating composition according to the invention may be obtained by mixing the constituents of the lubricating composition. The present invention also relates to a method for preparing a lubricating composition comprising the following steps:
  preparation of a composition of diesters according to the method described above; and
  mixing of at least one other base oil and/or at least one additive with the composition of diesters.

Preferably, the composition preparation method for preparing a lubricating composition according to the invention does not include an intermediate separation step of separating the products formed during the preparation of the composition of diesters, prior to the mixing.

The one or more other base oil(s) and the one or more additive(s) implemented in the method for preparing the lubricating composition may have one or more of the characteristic feature(s) described above in the context of the lubricating composition of the invention.

The lubricating composition obtained by this preparation method may exhibit one or more of the characteristic feature(s) described above in the context of the lubricating composition according to the invention.

Cosmetic or Pharmaceutical Composition

The object of the invention also relates to a cosmetic or pharmaceutical composition comprising: (i) the composition of diesters according to the invention; and (ii) at least one fatty substance; and/or (iii) at least one cosmetic additive.

Preferably, the composition of diesters used in the cosmetic or pharmaceutical composition has one or more of the characteristic feature(s) defined above in the context of the composition of diesters.

The composition of diesters exhibits improved physicochemical and sensory properties due to the intrinsic composition thereof, in addition to which, the composition of diesters according to the invention also exhibits very good miscibility with the other fatty substances conventionally used in the cosmetics or pharmaceutical fields. In particular, the composition of diesters according to the invention exhibits good miscibility with the fatty substances selected from among the group comprising of: hydrocarbon oils derived from biological or petrochemical sources, plant oils, plant butters, ethers and fatty alcohols, oily esters (other than diesters), alkanes, and silicone oils.

The fatty substance may be selected from among hydrocarbon oils derived from biological or petrochemical sources, plant oils, plant butters, ethers and fatty alcohols, oily esters (other than diesters), alkanes, and silicone oils.

Hydrocarbon oils are fatty substances that are derived from petrochemical processes. By way of example, mention may be made of mineral oils, isoparaffins, waxes, paraffins, polyisobutenes, or even polydecenes.

Examples of plant oils include in particular the following oils: wheat germ, sunflower, grapeseed, sesame, corn, apricot, castor, shea, avocado, olive, soy, sweet almond, palm, rapeseed, cottonseed, hazelnut, macadamia, jojoba, alfalfa, poppy, potimarron (red kuri squash), sesame, squash, rapeseed, blackcurrant, evening primrose oil, millet, barley, quinoa, rye, safflower, bankoulier, passion flower, muscat rose, or camellia. Plant butters are fatty substances that have the same properties as plant oils. The difference between the two lies in the fact that butters are in solid form at ambient temperature. Also, unlike plant oils, the raw material from which a butter is extracted (pulp, seeds, or kernels) is heated after being crushed in order to extract the fatty matter. Like plant oils, butters may be refined in order to ensure better preservation, neutralise odours, improve colour and consistency. Being nourishing and rich in antioxidants, the cosmetic properties of plant butters enhance the elasticity of the skin; protect it against the harmful effects of external or environmental elements by leaving a protective film over the epidermis and thus reducing dehydration; repair and soothe by regenerating the natural hydrolipidic film of the skin. Examples of plant butters are in particular shea butter, cocoa butter, mango butter, shorea butter, or even olive butter.

Fatty alcohols and ethers are waxy, long-chain fatty substances with remarkable properties including in particular film-forming, emollient, moisturising, softening and protective properties. They act as moisturising oils and as emulsifiers. Examples of fatty alcohol or ethers are: cetyl alcohol, stearyl alcohol, myristyl alcohol, auryl alcohol, behenyl alcohol, cetearyl alcohol, dicaprylyl ethers, stearyl ethers, or octyldodecanol (identified by their International Nomenclature of Cosmetic Ingredients (INCI) name).

The oily esters or esterified oils (separate and distinct from the diesters of the invention) are the product of a reaction between fatty acids (longer chain acids, such as for example stearic acid, oleic acid, palmitic acid) and alcohols (fatty alcohols or polyols such as glycerol). These oils may contain substances derived from petrochemicals, as is the case for Isopropyl Palmitate. Examples of oily esters are caprylic capric triglyceride, coco caprylate caprate, oleyl erucate, oleyl linoleate, decyl oleate, or even PPG-3 benzyl ether myristate (identified by their INCI name).

The term "silicone or polysiloxane oils" is understood to refer to an oil comprising at least one silicon atom, and in particular at least one Si—O group. By way of examples of silicone oil, mention may in particular be made of phenylpropyldimethylsiloxysilicate, dimethicones, or even cyclopentasiloxane (identified by their INCI name).

The additive, separate and distinct from the fatty substance and from the composition of diesters, may be selected from among any adjuvants or additives that are commonly used in the fields considered and in particular in the cosmetics, dermatological or pharmaceutical fields. Quite obviously, the person skilled in the art will seek to ensure the selection of the one or more possible additive(s) of the composition according to the invention in a manner such that the advantageous properties intrinsically attached to the emollient composition in accordance with the invention remain unaltered, or substantially unaltered by the addition envisaged. Among the conventional adjuvants that are likely to be contained (depending on the water-soluble or fat-soluble nature of these adjuvants), mention may be made in particular of: anionic foaming surfactants (such as sodium lauryl ether sulphate, sodium alkyl phosphate, sodium trideceth sulphate), amphoteric surfactants (such as alkyl betaine, disodium cocoamphodiacetate), or non-ionic surfactants with an HLB (hydrophilic-lipophilic balance) value greater than 10 (such as polyoxyethylene POE/Polypropylene glycol PPG/POE, Alkylpolyglucoside, polyglyceryl-3hydroxylauryl ether); preservatives; sequestering agents (EDTA); antioxidants; fragrances; dyestuffs such as soluble dyes, pigments and nacres; mattifying, tensor, whitening or exfoliating fillers; cosmetic active ingredients and agents that have the effect of enhancing the cosmetic properties of the skin, whether hydrophilic or lipophilic; electrolytes; polymers—hydrophilic or lipophilic, anionic, non-ionic, cationic, or amphoteric, thickeners, gelling agents, or dispersants; slimming agents such as caffeine; optical brighteners; anti-seborrheics; and mixtures thereof. The amounts of these various cosmetic adjuvants are those conventionally used in the field considered, and for example the cosmetic composition comprises an overall content ranging from 0.01 to 20% by weight of additives relative to the total weight of the composition.

In the case where the cosmetic, dermatological or pharmaceutical composition of the invention is a dermatological or pharmaceutical composition, the said composition may comprise one or more therapeutic active ingredients. By way of active agents that may be used in the dermatological or pharmaceutical composition of the invention, mention may be made, for example, of sunscreens; water-soluble or fat-soluble vitamins such as vitamin A (retinol), vitamin E (tocopherol), vitamin C (ascorbic acid), vitamin B5 (panthenol), vitamin B3 (niacinamide), derivatives of these vitamins (in particular esters) and mixtures thereof; antiseptics; antibacterial active ingredients such as 2,4,4'-trichloro-2'-hydroxy diphenyl ether (or triclosan), 3,4,4'-trichlorocarbanilide (or triclocarban); antimicrobials such as benzoyl peroxide, niacin (vit. PP); and mixtures thereof.

This cosmetic or pharmaceutical composition comprises a physiologically acceptable medium, that is to say which does not have deleterious side effects and in particular which does not produce effects that are unacceptable for users such as redness, heating, tightness or tingling.

According to one embodiment, the cosmetic, dermatological or pharmaceutical composition has a content of diester composition according to the invention ranging from 0.5 to 80%, preferably from 1 to 50% and advantageously from 5 to 30% by weight relative to the total weight of the cosmetic or pharmaceutical composition.

According to one embodiment of the invention, the cosmetic or pharmaceutical composition comprises, relative to the total weight of the cosmetic or pharmaceutical composition:
- from 0.5 to 80% by weight, preferably from 1 to 50% by weight and advantageously from 5 to 30% by weight, of the diester composition according to the invention;
- from 0 to 90% by weight, preferably from 5 to 80% by weight and advantageously from 10 to 70% by weight, preferably from 20 to 60% by weight, and advantageously from 30 to 50% by weight, of fatty substances;
- from 0 to 20% by weight of additives;
- from 0 to 20% by weight of therapeutic active ingredients;
- it being understood that the composition comprises at least one additive or at least one fatty substance.

According to one embodiment of the invention, the cosmetic or pharmaceutical composition comprises, relative to the total weight of the cosmetic or pharmaceutical composition:
- from 0.5 to 80% by weight, preferably from 1 to 50% by weight and advantageously from 5 to 30% by weight, of the diester composition according to the invention;
- from 0 to 90% by weight, preferably from 5 to 80% by weight and advantageously from 10 to 70% by weight, preferably from 20 to 60% by weight, and advantageously from 30 to 50% by weight, of fatty substances selected from among hydrocarbon oils derived from biological or petrochemical sources, plant oils, plant butters, ethers and fatty alcohols, oily esters (other than diesters), alkanes, and silicone oils;
- from 0 to 20% by weight of additives selected from among anionic, amphoteric or nonionic foaming surfactants with an HLB greater than 10; preservatives; sequestering agents; antioxidants; fragrances; dyestuffs; mattifying, tensor, whitening or exfoliating fillers; cosmetic active ingredients and agents that have the effect of enhancing the cosmetic properties of the skin, whether hydrophilic or lipophilic; electrolytes; polymers—hydrophilic or lipophilic, anionic, nonionic, cationic, or amphoteric, thickeners, gelling agents, or dispersants; slimming agents; optical brighteners; anti-seborrheics; and mixtures thereof;
- optionally from 0 to 20% by weight of therapeutic active ingredients;
- it being understood that the composition comprises at least one additive or at least one fatty substance.

The cosmetic or pharmaceutical composition according to the invention may thus be an anhydrous composition, an emulsion such as a water-in-oil (W/O) emulsion, an oil-in-water (O/W) emulsion, or a multiple emulsion (in particular W/O/W or O/W/O), a nano-emulsion, or even a dispersion.

The cosmetic or pharmaceutical composition according to the invention is in the form of a more or less soft cream or a vaporisable emulsion; it may constitute for example a make-up removal composition, or a skin cleansing or lip cleansing composition, an after-sun composition, a composition for massaging the skin, a shower care balm composition, an antiperspirant composition, a mask composition, a repairing balm composition, a scrub/peel and/or exfoliating composition for both the face and the hands (when it contains exfoliating particles), a make-up composition, a shaving composition, an after-shave balm composition, a perfumed composition, a composition for wipes, or indeed even a vaporisable composition.

The cosmetic or pharmaceutical composition according to the invention may also constitute a sunscreen composition when it includes at least one sunscreen.

The cosmetic or pharmaceutical composition according to the invention is a cosmetic composition when it provides only a cosmetic effect. Typically, the cosmetic composition according to the invention is free of therapeutic active ingredients.

In contrast, the cosmetic or pharmaceutical composition according to the invention is a dermatological or pharmaceutical composition when it provides a therapeutic effect. Typically, the dermatological or pharmaceutical composition according to the invention comprises at least one therapeutic active ingredient, for example selected from among sunscreens; antiseptics; antibacterial active ingredients such as 2,4,4'-trichloro-2'-hydroxy diphenyl ether (or triclosan), 3,4,4'-trichlorocarbanilide (or triclocarban); antimicrobials such as benzoyl peroxide, niacin (vit. PP); and mixtures thereof.

The cosmetic or pharmaceutical composition of the invention is advantageously characterised in that it exhibits a stability that is maintained over a period greater than or equal to 4 weeks, advantageously greater than or equal to 6 weeks, the stability being evaluated after storage without agitation at ambient temperature, at 40° C. and at 50° C., and corresponding to a visual evaluation of the colouring and of the appearance as well as an olfactory evaluation and/or a measurement of the viscosity.

Uses of the Cosmetic, Dermatological or Pharmaceutical Composition

The object of the invention further relates to the cosmetic or pharmaceutical use of the composition as defined above for topical application, for example on the skin, nails, lips, scalp, or hair.

The object of the invention also relates to the cosmetic or pharmaceutical use of the composition as defined above as: a skincare product (serums, creams, balms, etc), a hygiene product, a sunscreen/after-sun care product, a make-up product, a make-up remover, a perfumed product, an antiperspirant product.

The object of the invention further relates to a cosmetic or pharmaceutical treatment method for treating the skin, nails, lips, hair or scalp, that comprises at least one application step of applying to the skin, nails, lips, hair or the scalp a cosmetic or pharmaceutical composition as defined above.

The composition of diesters of the invention may also be used for the formulation of cosmetic compositions, dermatological compositions, or pharmaceutical compositions comprising various components or phases other than those described here above. This may in particular pertain to the formulation of care, hygiene or makeup compositions.

EXAMPLES

In the remainder of this description, examples are given by way of illustration of the present invention and are in no way intended to limit the scope thereof.

The term 'conversion' corresponds to the proportion expressed in percentage by weight of the unsaturated compound that has reacted.

The selectivity corresponds to the proportion expressed in percentage by weight of a desired specific diester (and of the positional isomers thereof) relative to the total weight of the diesters in the composition resulting from the method. In the examples following here below, the desired specific diester corresponds to a diester in which the branched saturated fatty acid is located at the level of the alcohol functional group of the unsaturated compound (after esterification reaction if the reactant is an unsaturated alcohol) and the linear fatty acid is located at the level of the carbon-carbon double bond of the unsaturated compound (after addition reaction according to the invention). In the remainder of the examples, when the unsaturated compound is an unsaturated alcohol ester, then the acid part of the ester is a branched acid.

In the examples here below:
"undecenol" refers to 10-undecenol.
"oleyl" refers to oleic alcohol.
"2EH" refers to 2-ethylhexanoic acid.
"C9" refers to nonanoic acid.
"C4" refers to butanoic acid.
"C7" refers to heptanoic acid.
"012" refers to lauric acid.
"3 MB" refers to 3-methylbutanoic acid.
"Oleyl-2EH" refers to the ester of 2-ethylhexanoic acid and oleic alcohol.
"undecenol-C9" refers to the ester of nonanoic acid and undecenol.
"PTSA" refers to para toluene sulfonic acid.
"Triflic" refers to triflic acid.
"Triflic/SiO2" refers to a triflic acid catalyst supported on silica.
"C9+2EH" refers to a composition comprising of nonanoic acid and 2-ethylhexanoic acid in a 2EH/C9 molar proportion of 1/4.
"C9+C12" refers to a composition comprising of nonanoic acid and lauric acid in a C9/C12 molar proportion of 3/3.
"P atm" indicates atmospheric pressure.
"Ratio" indicates the molar ratio of unsaturated compound/saturated acid(s)/catalyst.

The reactants and catalysts used are commercially available. The triflic acid catalyst supported on silica was prepared in the following manner:
Preparation of a suspension of 90.6 g of SiO2 in 315 mL of MTBE & adding of 7.4 g of triflic acid;
Stirring of the mixture for a period of one hour at ambient temperature, approximately 25° C. (pink colouration);
Concentration thereof followed by prolonged drying under reduced pressure for a period of 10 hours at 70° C. (obtaining of a powder).

The catalytic content of this supported catalyst is 0.50 mmol/g.

In the examples below, the progression of the reaction was monitored by gas chromatography coupled with a flame ionisation detector (GC-FID), for example with a DB5-HT column, according to methods that are well known to the person skilled in the art. The rates of conversion and selectivity may thus be determined.

Example 1: Implementation of a Method According to the Invention with a One-Step/Batch Mode Implementation In this example, the unsaturated compound and the one or more fatty acid(s) are introduced simultaneously and in their entirety. The catalyst and the operating conditions are indicated in Table 2 below.

TABLE 2

| | Unsaturated Compound | Fatty Acids | Catalyst | Ratio | T (° C.) and Pressure | Reaction Time (h) |
|---|---|---|---|---|---|---|
| Ex. 1 | Undecenol | 2EH | Triflic | 1/6/0.25 | 60° C. under vacuum | 24 |
| Ex. 2 | Undecenol | C9 | Triflic | 1/6/0.25 | 60° C. under vacuum | 24 |
| Ex. 3 | Oleyl-2EH | C9 | Triflic | 1/4/0.25 | 60° C. at P atm | 24 |
| Ex. 4 | Oleyl-2EH | C9 | Triflic | 1/4/0.25 | 60° C. at P atm | 7 |
| Ex. 5 | Oleyl-2EH | C9 | Triflic | 1/4/0.25 | 50° C. at P atm | 24 |
| Ex. 6 | Undecenol-C9 | C9 | Triflic | 1/4/0.25 | 60° C. at P atm | 8 |
| Ex. 7 | Undecenol | C9 + 2EH | Triflic | 1/6/0.25 | 60° C. under vacuum | 8 |
| Ex. 8 | Undecenol | C9 | Al(OTf)3 | 1/4/0.02 | 80° C. at P atm | 24 |
| Ex. 9 | Oleyl | C9 | Triflic/SiO2 | 1/5/0.3 | 83° C. at P atm | 72 |

The conversion rate and the selectivity are indicated in Table 3 below.

TABLE 3

| | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Conversion (%) | 87.0 | 85.3 | 69.1 | 63.9 | 70.3 | 80.8 | 83.0 | 70.0 | 58.5 |
| Selectivity (%) | NA | NA | 78.4 | 91.0 | 92.9 | NA | 63.5 | NA | NA |

In Table 3 above "NA" indicates "not applicable" since the same given saturated fatty acid was used to carry out the esterification reaction and the addition reaction. By default, the selectivity would be 100%.

It should be noted that the conversion rate may be increased by prolonging the duration of the reaction, in particular for the case where a single saturated fatty acid is implemented, since there is no problem of transesterification in this embodiment. The reaction time may thus be adjusted in order to achieve a good compromise between the conversion rate and selectivity towards the desired diester.

These examples show that the method according to the invention makes it possible to obtain both very good selectivity towards the desired diester and a very good conversion rate.

It may be noted, for examples Ex.3, Ex.4 and Ex.5, a very good selectivity rate, of at least 78% towards the desired diester, that is to say the diester obtained by adding the nonanoic acid across the carbon-carbon double bond of 2-ethylhexanoic acid ester and oleic alcohol. The selectivity rate is less than 100% since diesters resulting from transesterification reactions may be formed.

Example Ex.7 provides the means to obtain a random mixture of diesters since the two fatty acids introduced can react either on the alcohol functional group or on the olefin functional group.

Example 2: Implementation of Another Method According to the Invention with a Two-Step/Sequential Mode Implementation In this example, the unsaturated compound is caused to be reacted with a first fatty acid (fatty acids 1) at the initial stage in the presence of a catalyst of a type such as PTSA and under conditions 1 (ratio 1, temperature and pressure 1, and time 1); thereafter, without an intermediate isolation step, a second fatty acid (fatty acids 2) is introduced into the mixture obtained in the presence of a catalyst of a type such as triflic acid and under conditions 2 (ratio 2, temperature and pressure 2 and time 2). The reactants and conditions 1 and 2 are indicated in Table 4 below.

The conversion rate and the selectivity are indicated in Table 5 below.

TABLE 5

|  | Ex. 10 | Ex. 11 | Ex. 12 |
| --- | --- | --- | --- |
| Conversion (%) | 58.6 | 82.9 | 78.9 |
| Selectivity (%) | 85.4 | 98.4 | NA |

In Table 5 above "NA" indicates "not applicable" since the same given acid was used to carry out the esterification reaction and the addition reaction.

The method according to the invention makes it possible to obtain a desired specific diester with excellent selectivity given that the rate is at least 85% according to the results in Table 5, even without an intermediate isolation step for isolating the unreacted acids or the undesired esters formed in the first step.

Example 3: Implementation of Another Method According to the Invention with a Two Step/Batch Mode Implementation In this example, the first step consists of an esterification step: 1 molar equivalent of the unsaturated compound is caused to be reacted with approximately 1.1 molar equivalent of a first fatty acid (fatty acids 1) at the initial stage in the presence of a catalyst of a type such as PTSA (0.02 molar equivalent) and under standard esterification conditions (toluene with azeotrope entrainment in order to remove water).

Thereafter, the composition resulting from the first esterification step is washed in order to remove the catalyst, according to well-known conventional techniques (for example with distilled water and optionally NaCl if the two phases are difficult to separate, in multiple steps), and then the organic phase is dried and filtered. The washed composition (organic phase) was then distilled by vacuum distillation (stripping) in order to remove the excess saturated fatty acid.

Then, the purified composition (predominantly comprising unsaturated monoesters) is caused to be reacted with a saturated fatty acid (fatty acid 2) in the presence of a catalyst of a type such as triflic acid and under the conditions described in Table 6 below, in order to carry out the addition reaction for addition of the acid across the carbon-carbon double bond.

TABLE 4

|  | Unsaturated Compound | Fatty Acids 1/ Fatty Acids 2 | Ratio 1-Ratio 2 | T(° C.) and Pressure 1/T(° C.) and Pressure 2 | Time(h) 1/ Time(h) 2 |
| --- | --- | --- | --- | --- | --- |
| Ex. 10 | Oleyl | 2EH/09 | 1/1.1/0.02-1/4/0.25 | 90° C. under vacuum/ 60° C. at P atm | 24/8 |
| Ex. 11 | Undecenol | 2EH/09 | 1/1.1/0.02-1/4/0.25 | 90° C. under vacuum/ 60° C. at P atm | 24/8 |
| Ex. 12 | Undecenol | 09/09 | 1/1.1/0.02-1/4/0.25 | 90° C. under vacuum/ 60° C. at P atm | 24/8 |

TABLE 6

|  | Unsaturated Compound | Fatty Acids 1/ Fatty Acids 2 | Ratio | T(° C.) and Pressure (Step 2) | Time(h) (Step 2) |
|---|---|---|---|---|---|
| Ex. 13 | Undecenol | 2EH/C4 | 1/6/0.25 | 60° C. at P atm | 8 |
| Ex. 14 | Undecenol | 2EH/C7 | 1/6/0.25 | 60° C. at P atm | 8 |
| Ex. 15 | Undecenol | 3MB/C7 | 1/6/0.25 | 60° C. at P atm | 8 |
| Ex. 16 | Undecenol | 2EH/C12 | 1/6/0.25 | 60° C. at P atm | 8 |
| Ex. 17 | Undecenol | 3MB/C12 | 1/6/0.25 | 60° C. at P atm | 8 |
| Ex. 18 | Undecenol | 2EH/C9 | 1/6/0.25 | 60° C. at P atm | 8 |
| Ex. 19 | Undecenol | 3MB/C9 | 1/6/0.25 | 60° C. at P atm | 8 |
| Ex. 20 | Undecenol | C9/C9 | 1/6/0.25 | 60° C. at P atm | 8 |
| Ex. 21 | Undecenol | 3MB/(C9 + C12) | 1/6/0.25 | 60° C. at P atm | 8 |
| Ex. 22 | Oleyl | 2EH/C12 | 1/6/0.25 | 60° C. at P atm | 8 |
| Ex. 23 | Oleyl | 3MB/C12 | 1/6/0.25 | 60° C. at P atm | 8 |
| Ex. 24 | Oleyl | 2EH/C9 | 1/6/0.25 | 60° C. at P atm | 8 |
| Ex. 25 | Oleyl | 3MB/C12 | 1/4/0.25 | 60° C. at P atm | 8 |
| Ex. 26 | Oleyl | 2EH/C9 | 1/4/0.25 | 60° C. at P atm | 8 |

The conversion rate and the selectivity are indicated in Tables 7 and 8 below.

TABLE 7

|  | Ex. 13 | Ex. 14 | Ex. 15 | Ex. 16 | Ex. 17 | Ex. 18 | Ex. 19 |
|---|---|---|---|---|---|---|---|
| Conversion (%) | 85.4 | 82.3 | 83.2 | 86.2 | 81.5 | 79.5 | 81.5 |
| Selectivity (%) | 99.5 | 100 | 98.3 | 99.4 | 100 | 99.6 | 98.5 |

TABLE 8

|  | Ex. 20 | Ex. 21 | Ex. 22 | Ex. 23 | Ex. 24 | Ex. 25 | Ex. 26 |
|---|---|---|---|---|---|---|---|
| Conversion (%) | 80.2 | 78.6 | 62.0 | 63.0 | 62.7 | 64.1 | 62.2 |
| Selectivity (%) | NA | ND | 91.1 | 89.6 | 95.3 | 92.8 | 95.1 |

In Tables 7 and 8 above:

"NA" indicates "not applicable" since the same given acid was used to carry out the esterification reaction and the addition reaction.

"ND" indicates that the selectivity has not been determined.

As illustrated in Tables 7 and 8, the method according to the invention makes it possible to obtain diesters with an excellent conversion rate and excellent selectivity towards the desired diester, that is to say where the branched fatty acid has reacted on the alcohol functional group of the unsaturated compound in order to obtain an unsaturated monoester and where the linear saturated fatty acid has reacted across the carbon-carbon double bond of the unsaturated monoester.

Example 4: Lubricating Properties of the Compositions of Diesters According to the Invention The compositions of diesters (Ex.1, Ex.11 to Ex.26) obtained in Examples 1 to 3 were then purified in order to eliminate the reactants that remain unreacted as well as any unsaturated alcohol monoesters formed. This purification was carried out by means of stripping.

The lubricating properties of these compositions thus purified were evaluated.

The kinematic viscosity in mm$^2$/s of the compositions of diesters according to the invention was determined at 40° C. (KV40) and at 100° C. (KV100) according to the standard ASTD D7042.

The Noack volatility was measured according to the standard ASTM D6375.

The pour point (PP) was determined according to the standard ASTM D7346.

These properties are reported in Tables 9 and 10 below.

TABLE 9

|  | Ex. 1 | Ex. 11 | Ex. 12 | Ex. 13 | Ex. 14 | Ex. 15 | Ex. 16 | Ex. 17 | Ex. 18 |
|---|---|---|---|---|---|---|---|---|---|
| KV40 | 12.48 | 13.90 | 15.14 | 9.505 | 11.38 | 9.81 | 17,86 | 15.31 | 13.20 |
| KV100 | 3.290 | 3.570 | 3.988 | 2.685 | 3.103 | 2.868 | 4.307 | 3.990 | 3.452 |
| Noack | 16.0 | 9.0 | 6.3 | 28.2 | 15.8 | 28.2 | 4.1 | 7.6 | 10.5 |
| PP (° C.) | −74 | −75 | −18 | −81 | −78 | −63 | −48 | −21 | −75 |

TABLE 10

|  | Ex. 19 | Ex. 20 | Ex. 21 | Ex. 22 | Ex. 23 | Ex. 24 | Ex. 25 | Ex. 26 |
|---|---|---|---|---|---|---|---|---|
| KV40 | 11.37 | 14.68 | 13.99 | 30.65 | 25.26 | 24.61 | 21.68 | 21.72 |
| KV100 | 3.214 | 3.945 | 3.720 | 5.320 | 4.991 | 4.886 | 6.227 | 5.523 |
| Noack | 16.4 | 6.3 | 10.6 | 2.4 | 3.6 | 3.8 | 4.8 | 4.2 |
| PP (° C.) | −57 | −21 | −30 | −27 | −21 | −52 | −24 | −51 |

The above properties show that the diester compositions according to the invention exhibit suitable properties such that they may be used as base oil in lubricating compositions.

Example 5: Evaluation of the Cosmetic Properties

The composition of diesters Ex.25 was evaluated in respect of sensory properties.

The following properties were evaluated by a panel of professionals and the results are indicated in Table 11:
- penetration over the skin: if the product penetrates well, the result is OK and if the product does not penetrate well, the result is NOK;
- gloss: if the product is glossy, the result is OK and if the product is not glossy, the result is NOK;
- irritation: if the product does not cause irritation, the result is OK and if the product causes irritation, the result is NOK
- greasy feeling on the skin: if the product does not leave a greasy feeling, the result is OK and if the product leaves a greasy feeling, the result is NOK.

TABLE 11

|  | Penetration | Gloss | Irritation | Greasy Feeling |
|---|---|---|---|---|
| Ex. 25 | OK | OK | OK | OK |

The results of Table 11 show that the compositions of diesters according to the invention have good sensory properties, thereby making them suitable to be used in cosmetic or pharmaceutical compositions for topical applications meant for the skin, nails, lips, hair or scalp.

We claim:

1. A method for preparing a composition of diesters comprising at least one addition reaction of an acid functional group of at least one saturated fatty acid containing from 2 to 18 carbon atoms on a carbon-carbon double bond of at least one unsaturated compound selected from among an unsaturated alcohol containing from 11 to 20 carbon atoms, an ester of a saturated fatty acid containing from 2 to 18 carbon atoms and of an unsaturated alcohol containing from 11 to 20 carbon atoms, or a mixture thereof, in the presence of at least one acid catalyst, wherein the unsaturated alcohol or the ester thereof is derived from plant or animal oils.

2. The method according to claim 1, wherein the unsaturated alcohol is a monounsaturated monoalcohol containing from 11 to 18 carbon atoms and/or the saturated fatty acid, used in the addition reaction and/or in the acid part of the unsaturated compound in ester form, is a monofatty acid containing from 2 to 16 carbon atoms.

3. The method according to claim 1, wherein the unsaturated compound comprises at least one unsaturated alcohol, the said method comprising the following two reactions:
   a) Esterification reaction causing esterification of at least one unsaturated alcohol containing from 11 to 20 carbon atoms with at least one saturated fatty acid, either linear or branched, containing from 2 to 18 carbon atoms, in order to obtain at least one ester of the unsaturated alcohol; and
   b) Addition reaction of at least one saturated fatty acid, either linear or branched, containing from 2 to 18 carbon atoms, on the carbon-carbon double bond of the one or more unsaturated alcohol ester(s) obtained at the end of step a).

4. The method according to claim 1, wherein the addition reaction of the saturated fatty acid on the unsaturated compound is carried out in accordance with one or more of the following conditions:
- at a temperature ranging from 20 to 90° C.; and/or
- at atmospheric pressure or under vacuum; and/or
- a molar ratio of the unsaturated compound/saturated fatty acid ranging from 1/10 to 1/1; and/or
- a molar ratio of the unsaturated compound/catalyst ranging from 1/0.05 to 1/1.

5. The method according to claim 1, wherein the unsaturated compound is an unsaturated alcohol, the said method being implemented:
- in one single batch step with introduction of the entirety of the saturated fatty acids used in the method; or
- in two steps, including a first step of introducing a portion of the fatty acids, in order to carry out the esterification of the unsaturated alcohol(s), followed by a second step of introducing the rest of the saturated fatty acids, in order to carry out the addition reaction.

6. A composition of diesters that is obtainable by the method according to claim 1, comprising at least one compound having the formula (1):

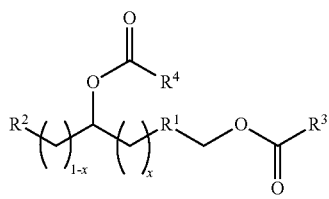

[Chem 1]

wherein:
R$^1$ is a linear or branched alkylene or alkenylene radical containing from 3 to 15 carbon atoms;
R$^2$ is a hydrogen atom or a linear or branched alkyl or alkenyl radical containing from 1 to 16 carbon atoms;
R$^3$ and R$^4$ are, independently of each other, a linear or branched alkyl radical containing from 1 to 17 carbon atoms;
x is an integer equal to 0 or 1;
it being understood that the sum of the carbon atoms of the radicals R$^1$ and R$^2$ ranges from 8 to 17.

7. A lubricating composition comprising the composition of diesters according to claim 6 and at least one base oil and/or at least one additive, the said base oil and the said additive being other than the diesters according to claim 6.

8. A cosmetic or pharmaceutical composition comprising the composition of diesters according to claim 6 and at least one fatty substance and/or at least one additive, the said fatty substance and the said additive being other than the diesters according to claim 6.

9. The method according to claim 2, wherein the unsaturated alcohol is a monounsaturated monoalcohol containing from 14 to 18 carbon atoms and/or the saturated fatty acid, used in the addition reaction and/or in the acid part of the unsaturated compound in ester form, is a monofatty acid containing from 7 to 12 carbon atoms.

10. The method according to claim 3, wherein step a) is performed with at least one branched saturated fatty acid, and/or step b) is performed with at least one linear saturated fatty acid.

11. The method according to claim 4, wherein the addition reaction of the saturated fatty acid is performed on the ester of the unsaturated alcohol.

12. The method according to claim 4, wherein the addition reaction is carried out in accordance with one or more of the following conditions:
at a temperature ranging from 30 to 85° C.; and/or
at atmospheric pressure; and/or
a molar ratio of the unsaturated compound/saturated fatty acid ranging from 1/8 to 1/2; and/or
a molar ratio of the unsaturated compound/catalyst ranging from 1/0.1 to 1/0.8.

13. The method according to claim 4, wherein the addition reaction is carried out in accordance with one or more of the following conditions:
at a temperature ranging from 40 to 80° C.; and/or
a molar ratio of the unsaturated compound/saturated fatty acid ranging from 1/7 to 1/3; and/or
a molar ratio of the unsaturated compound/catalyst ranging from 1/0.15 to 1/0.5.

14. The method according to claim 5, implemented in two steps, including a first step of introducing a portion of the fatty acids, in order to carry out the esterification of the unsaturated alcohol(s), followed by a second step of introducing the rest of the saturated fatty acids, in order to carry out the addition reaction,
wherein these two steps are implemented sequentially without separation of the esters obtained at the end of the esterification reaction.

15. A method for preparing a composition of diesters comprising at least one addition reaction of an acid functional group of at least one saturated fatty acid containing from 2 to 18 carbon atoms on a carbon-carbon double bond of at least one unsaturated compound selected from among an unsaturated alcohol containing from 11 to 20 carbon atoms, an ester of a saturated fatty acid containing from 2 to 18 carbon atoms and of an unsaturated alcohol containing from 11 to 20 carbon atoms, or a mixture thereof, in the presence of at least one acid catalyst, said composition comprising at least one compound having the formula (1):

[Chem 1]

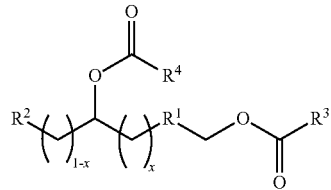

wherein:
$R^1$ is a linear or branched alkylene or alkenylene radical containing from 3 to 15 carbon atoms; $R^2$ is a hydrogen atom or a linear or branched alkyl or alkenyl radical containing from 1 to 16 carbon atoms;
$R^3$ and $R^4$ are, independently of each other, a linear or branched alkyl radical containing from 1 to 17 carbon atoms;
x is an integer equal to 0 or 1;
it being understood that the sum of the carbon atoms of the radicals $R^1$ and $R^2$ ranges from 8 to 17.

* * * * *